(12) United States Patent
Sattler et al.

(10) Patent No.: US 7,015,808 B1
(45) Date of Patent: Mar. 21, 2006

(54) METHOD AND SYSTEM FOR REMOTE MONITORING OF PROCESSING STATUS IN COMPUTER-AIDED DETECTION SYSTEMS

(75) Inventors: Jason Sattler, Beavercreek, OH (US); Terry Dolwick, Enon, OH (US); Telford Berkey, London, OH (US); Thomas Fister, Lebanon, OH (US)

(73) Assignee: ICAD, Inc., Beavercreek, OH (US)

( * ) Notice: Subject to any disclaimer, the term of this patent is extended or adjusted under 35 U.S.C. 154(b) by 187 days.

(21) Appl. No.: 10/769,315

(22) Filed: Jan. 30, 2004

Related U.S. Application Data

(60) Provisional application No. 60/444,919, filed on Feb. 4, 2003.

(51) Int. Cl.
*G08B 1/00* (2006.01)
*H04Q 1/30* (2006.01)

(52) U.S. Cl. .................. 340/531; 340/539.12; 382/132

(58) Field of Classification Search ................ 340/531, 340/539.12, 539.17, 539.18; 128/903; 382/132, 382/173
See application file for complete search history.

(56) References Cited

U.S. PATENT DOCUMENTS

| | | | |
|---|---|---|---|
| 5,224,177 A * | 6/1993 | Doi et al. ................... | 382/168 |
| 5,586,160 A * | 12/1996 | Mascio ........................ | 378/37 |
| 5,917,929 A | 6/1999 | Marshall et al. | |
| 6,031,929 A * | 2/2000 | Maitz et al. ................ | 382/132 |
| 6,198,394 B1 * | 3/2001 | Jacobsen et al. ......... | 340/573.1 |
| 6,621,413 B1 * | 9/2003 | Roman et al. ......... | 340/539.12 |
| 6,727,814 B1 * | 4/2004 | Saltzstein et al. ........... | 340/531 |
| 6,895,128 B1 * | 5/2005 | Bohnenkamp .............. | 382/305 |

* cited by examiner

*Primary Examiner*—John Tweel, Jr.
(74) *Attorney, Agent, or Firm*—Dinsmore & Shohl LLP

(57) ABSTRACT

This invention relates to a method and system for remotely monitoring computer-aided detection (CAD) system processing status. In film-based CAD systems digital images are created by a film digitizer, which is typically loaded with 50 or 100 films. Occasionally, film feeding errors occur which halt the digitization. This invention provides a method and system for detecting the stoppage and for notifying an operator who is not in the vicinity of the digitizer. Notification is accomplished by a variety of methods including pager, telephone, cell phone, and mobile computing devices. In addition to notification of stoppages, the operator may choose to be notified when a certain number of films remain to be processed. This allows the digitizer to be loaded with additional films before the CAD system completes processing of the originally loaded set of films. System efficiency is increased by eliminating idle intervals where the CAD system is stopped awaiting input data.

31 Claims, 6 Drawing Sheets

```
<operator_id>
        %op_id%

<channel_preference>
        %preferred_channel_1%
        %preferred_channel_2%

<low_film_warn>
        %low_film_yes_no%

<pager>
        %pager_number%
        %error_code%

<email>
        %email_address_1%
        %email_address_2%
        %e_notify_msg%
        %worklist%

<voice_phone>
        %voice_number%
        %v_notify_msg%

<enabled_phone>
        %enabled_phone_number%
        %ep_notify_msg%
        %worklist%

<network>
        %username%
        %net_notify_msg%
```

To: Technologist 3
From: CAD system 5
Time and Date: 0215, 7 Feb 03

- Halt on case 3 of 25 at 2:15 am on February 7, 2003
- 87 of 100 films remain in input tray of CAD system 5
- Worklist Information

| Patient Name | Status |
|---|---|
| Patient 1 | Complete |
| Patient 2 | Complete |
| Patient 3 | Halted |
| Patient 4 | Pending |
| Patient 5 | Pending |
| . | |
| . | |
| . | |
| Patient 25 | Pending |

Fig. 6

METHOD AND SYSTEM FOR REMOTE MONITORING OF PROCESSING STATUS IN COMPUTER-AIDED DETECTION SYSTEMS

CROSS-REFERENCE TO RELATED APPLICATIONS

This application claims the benefit of U.S. Provisional application Ser. No. 60/444,919 filed Feb. 4, 2003, incorporated herein by reference.

BACKGROUND OF THE INVENTION

1. Field of the Invention

This invention relates to a method and system for remotely monitoring processing status in computer-aided detection (CAD) systems.

2. Discussion of Related Prior Art

Medical CAD systems are commercially available to assist in the detection of breast and lung cancer, including products by iCAD Inc. (Hudson, N.H.) and Deus Technologies (Rockville, Md.). CAD systems process digital versions of medical images to produce an output indicating potentially cancerous regions. When the medical image is a film, a film digitizer is used to create the digital image. In practice, operators use CAD systems to process hundreds of films each day by way of batch feeding, where many films are placed in an input tray, then mechanically fed into the digitizer. The CAD system operator typically has many other duties at locations where the CAD system is not visible, and does not monitor the digitization process.

A typical CAD system configuration is shown in FIG. 1. System components are housed in a console, comprising a film digitizer, computer, and monitor. The film feeding process is susceptible to failure from situations such as double feeds or jams. Furthermore, digitizers may issue firmware error codes when internal device errors cause the digitization process to halt. When an error in digitization occurs, a message corresponding to the error code may be displayed on the monitor. Current systems can notify only an operator near the monitor. Consequently, when the operator returns to the CAD system and the message received by the operator, processing has been stopped for an interval of time. Any stoppage in film feeding is costly in terms of lost processing time.

Consider the situation of an operator starting a batch process of 25 cases near the end of the workday. The operator loads the films into the digitizer and initiates CAD processing. If a film happens to jam after the first case, the remaining 24 cases must be processed the next day. Assuming the system requires an average of 5 minutes to process a case, it will take 2 hours to complete running CAD for these cases.

The primary purpose of CAD systems is to assist radiologists in the detection of cancer. However, radiologists also face economic realities and CAD systems are costly medical devices. In the United States, the federal government provides reimbursement for each mammographic study read with CAD assistance. It is sound business practice to maximize the number of studies provided to the CAD system.

The introduction of CAD equipment to clinics has increased the workload for radiological technologists. Radiological technologists working in mammography clinics are responsible for a variety of tasks of including exposing mammograms, developing films, and keeping associated records, all while maintaining efficient workflow. The technologist does not have the time to monitor the digitization process at the CAD system. Yet, the medical benefits of timely availability of CAD results for the patient, and the economic benefits of a continuously running CAD machine require the digitization process be kept running.

Given the economic and workflow factors, it is therefore desirable to provide a method and system to provide CAD processing status information to an operator who is remotely located from the CAD system.

SUMMARY OF THE INVENTION

The present invention provides a method and system for remotely monitoring computer-aided detection system processing status. Specifically, the present invention provides of notification of a remotely located user in the event that a delay or stoppage of a system for performing CAD processing of images is detected.

In one aspect of the invention, a method is provided for remote monitoring of status information to a film-based CAD system user comprising: providing a CAD system with a film digitizer; providing films to be processed to the film digitizer; performing a processing operation on the films; identifying a status change in the digitizer during the processing operation; and transmitting notification of the status change to a user located remotely from the digitizer.

In another aspect of the invention, a method is provided for operating a digitizer comprising: providing a CAD system, the CAD system including a film digitizer and a user specific configuration file having information for initiating contact with a user; providing films to be processed to the film digitizer; performing a processing operation on the films; identifying a status change in the digitizer during the processing operation; and transmitting notification of the status change to a user located remotely from the digitizer.

In a further aspect of the invention, a method is provided for remote monitoring of status information to a film-based CAD system user comprising: providing a CAD system with a film digitizer; providing films to be processed to the film digitizer; performing a processing operation on the films; identifying a status change in the digitizer during the processing operation; and initiating contact with a user located remotely from the digitizer in response to the identification of a status change.

In yet another aspect of the invention, a method is provided for remote monitoring of status information to a CAD system user comprising: providing input imagery to the CAD system; performing a processing operation on the input imagery; identifying a status change in the processing operation; and transmitting notification of the status change to a user located remotely from the CAD system.

Other objects and advantages of the invention will be apparent from the following description, the accompanying drawings and the appended claims.

BRIEF DESCRIPTION OF THE DRAWINGS

FIG. 3 illustrates an exemplary operator config file;

FIG. 6 illustrates an exemplary notification.

DETAILED DESCRIPTION OF THE PREFERRED EMBODIMENT

Figure 1:
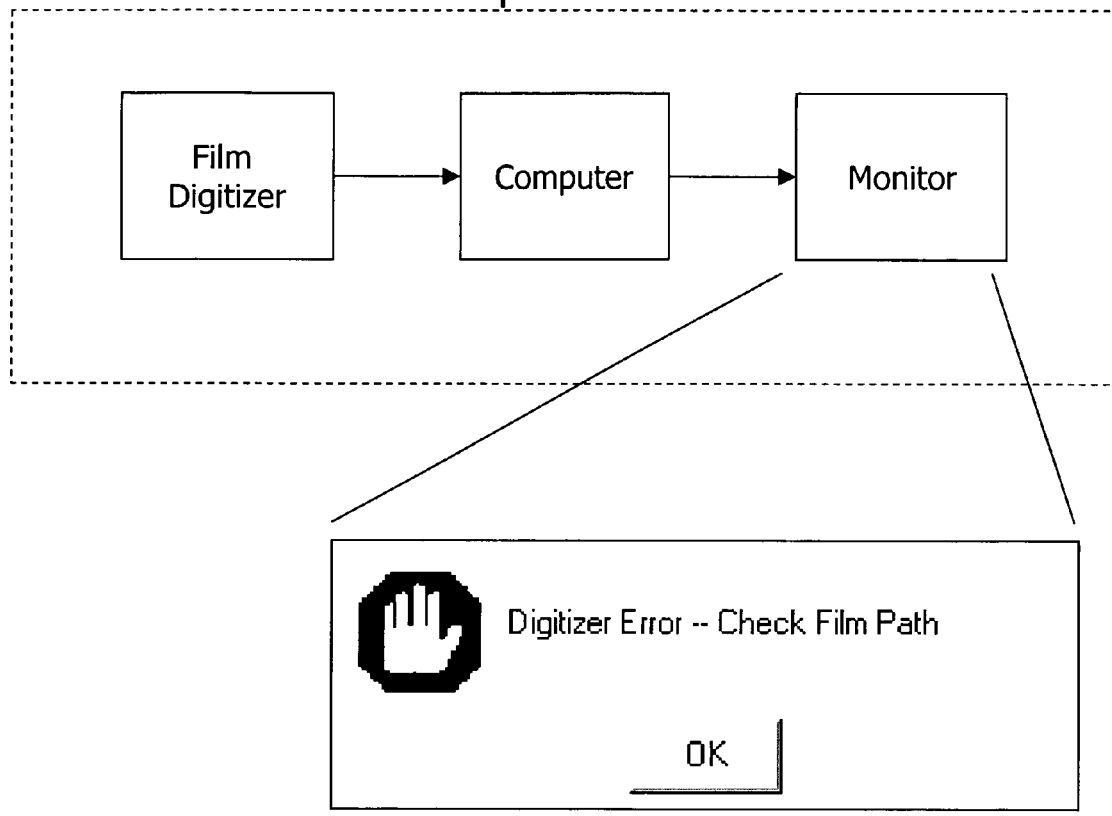
FIG. 1 diagrammatically illustrates a prior art system displaying a processing status message on an operator console.
Figure 2:
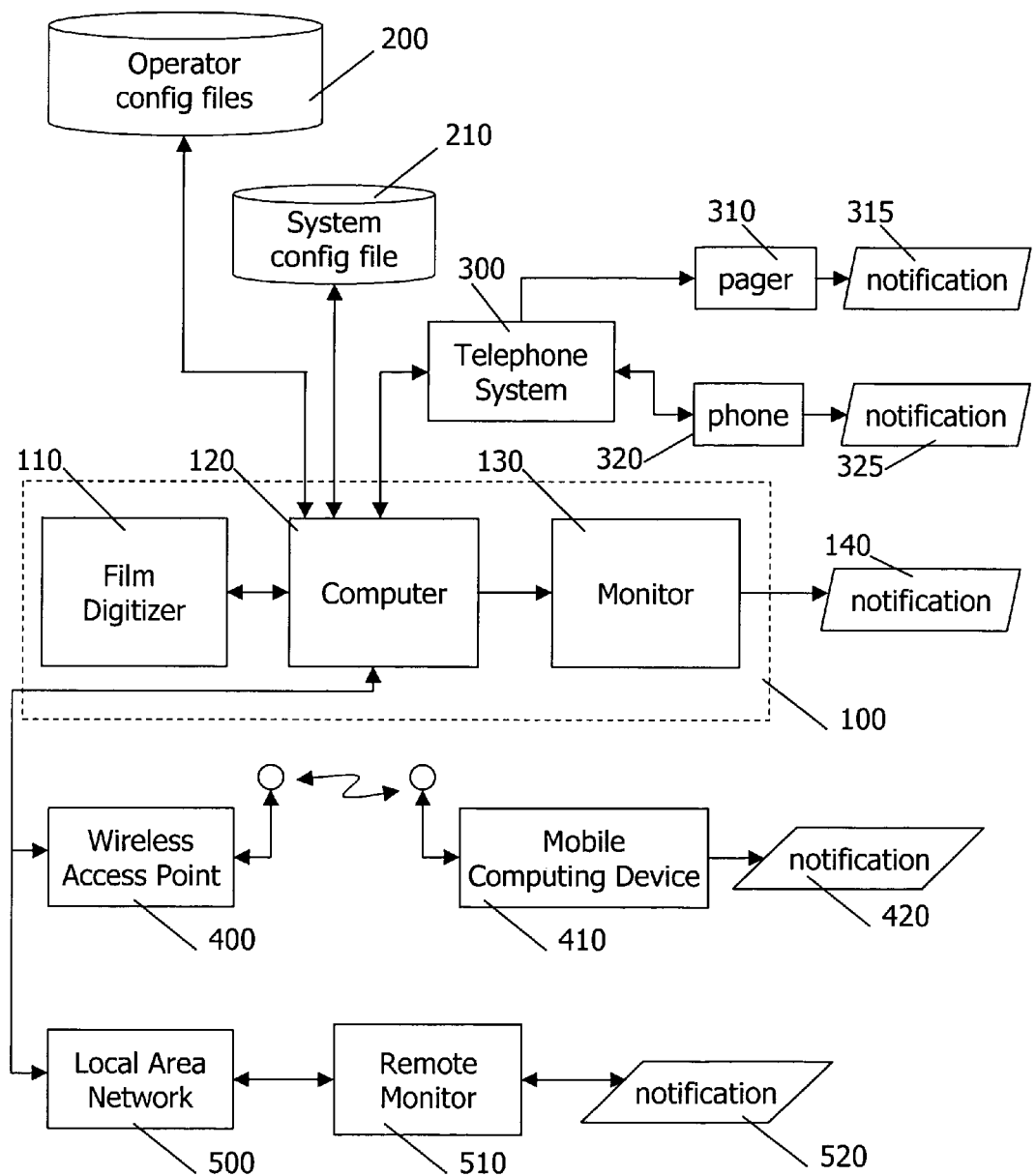
FIG. 2 diagrammatically illustrates the overall architecture of the present invention.

An overview of the invention is provided in FIG. 2. The CAD system console 100, comprises a housing for film digitizer 110, a computer 120, and a monitor 130. The computer in the CAD system console is provided with a variety of communication devices, comprising telephonic connection 300, a wireless access point 400, and a local area network 500. Operator config files 200, contains operator specific address information, such as pager and telephone numbers, email address, IP address, preference of notification details, and delivery options. A system config file 210 contains information specific to the network communication paths and a CAD system notification option.

When an event occurs that halts CAD processing, a notification is transmitted to one or more operators via the method specified in the operator configuration files. Notifications can be in the form of a simple message, such as a message box displayed on a screen. Alternatively, notification can provide detailed information, such as a hypertext document including the number of cases or films remaining to be processed, the time and nature of the halt, and so on.

In the case of telephonic notification to an operator's pager 310, notification 315 is a text message. In the case of notification by phone 320, notification 325 is a voice message. The pager and phone may be caller-ID enabled, and in this situation, the operator is assumed to recognize the calling number. Therefore, the operator would know to check the CAD processing when a call is received from the CAD system. Alternatively, the operator may choose to listen to additional information provided in a voice message. In a preferred embodiment, the operator is first notified by a caller-ID enabled device and has the option of requesting further information.

In facilities with a remote area network 500 and monitors 510 in multiple locations, the notification may be sent to remote monitors according to a predetermined preference specified in a configuration file. In a preferred embodiment, a notification of a halt in processing 520 is displayed on a predetermined set of monitors. In another embodiment, the notification is broadcast only to the monitor(s) currently in use by a predetermined set of operators. Alternatively, notification 520 is an email message notifying an operator of a halt in processing.

In facilities with wireless networks, a wireless access point 400, communicates with a user's mobile computing device 410, to display a notification 420. Mobile computing devices comprise personal digital assistants, wireless-enabled laptop computers and cell phones with wireless internet capability. Notification 420 can be in the form of a message box displayed on screen or an email message.

Preferably, worklist information is made available to the remotely located operator. A worklist is a set of patient identifiers with case information, processing status and operator identification. The set of patient identifiers corresponds to the collection of films input to the CAD system. Case information includes the number of films in the case. Processing status can be "pending", "in progress", "halted", or "completed". The worklist may be conveyed in an ASCII or hypertext formatted email message.

Operator Config File

Operator config files are used to specify delivery option, message content and operator address information. An operator config file contains operator specific address information, such as pager or phone numbers, email address, IP address, preference of notification details, and delivery options. A format for an operator config file is shown in FIG. 3, 299. Fields in the operator config file are indicated within angled brackets (< >) and variable names are shown between percent signs (%).

Two fields in an operator config file determine the identity and notification channels for the associated operator. The operator identity is stored under the field labeled <operator_id>. The variable storing identity related information of the operator is % op_id %. Preferred notification channels are determined by reading values for variables under the <channel_preference> field. Since an operator may desire to be notified by more than one method, the channel preference field is allowed to contain more than one entry. In this example, allowed values for % preferred_channel_n % include: "pager", "email", "voice_phone", "enabled_phone", and "network". A third field, <low_film_warn> indicates whether or not the operator wishes to be notified when a predetermined minimum number of films remain to be processed. The variable % low_film_yes_no % stores the "yes" or "no" option according to the operators wishes.

Subsequent fields in the operator config file specify address information and message content settings. The <pager> field contains a variable storing the telephone number of the pager, % pager_number %. In a preferred embodiment, the option to transmit an alphanumeric error code is provided by the variable % error_code %. The value of this variable is obtained from a halt code provided by the CAD system. The <email> field contains variables for one or more email addresses, % email_address_n %, where the operator desires notification messages to be sent, as indicated by variables % email_address_1% and % email_address_2%. Message content of the email notification is determined by providing one or more variable names. Here, % e_notify_msg % indicates a text message suitable for email is to be populated by parsing a halt code provided by the CAD system. Additionally, the worklist information can be provided by storage and transmission of the variable % worklist %.

Parameters for a voice-only telephonic notification are provided under the <voice_phone> field. The telephone number is stored in the variable % voice_number %, and elements in the voice message are determined by the contents of the variable % v_notify_msg %. The contents of % v_notify_msg % are later parsed by a text-to-speech or other application for conveying textual information telephonically.

Parameters for a web-enabled telephone are provided under the <enabled_Phone> field. The telephone number is stored in the variable % enabled_phone_number %. Message content is determined by providing one or more variable names. In this example, the notification will consist of values stored in the % ep_notify_msg % variable along with worklist information in the % worklist % variable. It is also possible for the variable % v_notify_msg % to be stored under the <enabled_phone> field for audio delivery of selected information.

Notifications may also be provided over network connections according to information specified under the <network> field. The network identification of the operator is stored in the variable % username %. Content of the notification is determined by providing one or more variable names. In this example, the message is stored in the variable % net_notify_msg %.

System Config File

The system config file 210 contains site specific information. This information includes dialing options for modem operations. For example, whether or not a '9' must be dialed to reach an outside line. Similarly, network communication information may also be stored in the system config file. Additionally, the system config file stores a value, N_low, used to specify a value for a "low film count" at the input of the CAD system. Operators can choose to be notified when the low film count limit is reached by specifying an option in their operator config file.

Halt Detection

Halted processing is detected by an automated method. The method first initializes variables indicating the status of the process and the elapsed time status. Then, if the elapsed time status indicates a time interval has been exceeded while the process status is indicating an unfinished process, a halt notification is sent to a user. A detailed description of operation follows.

Figure 4:
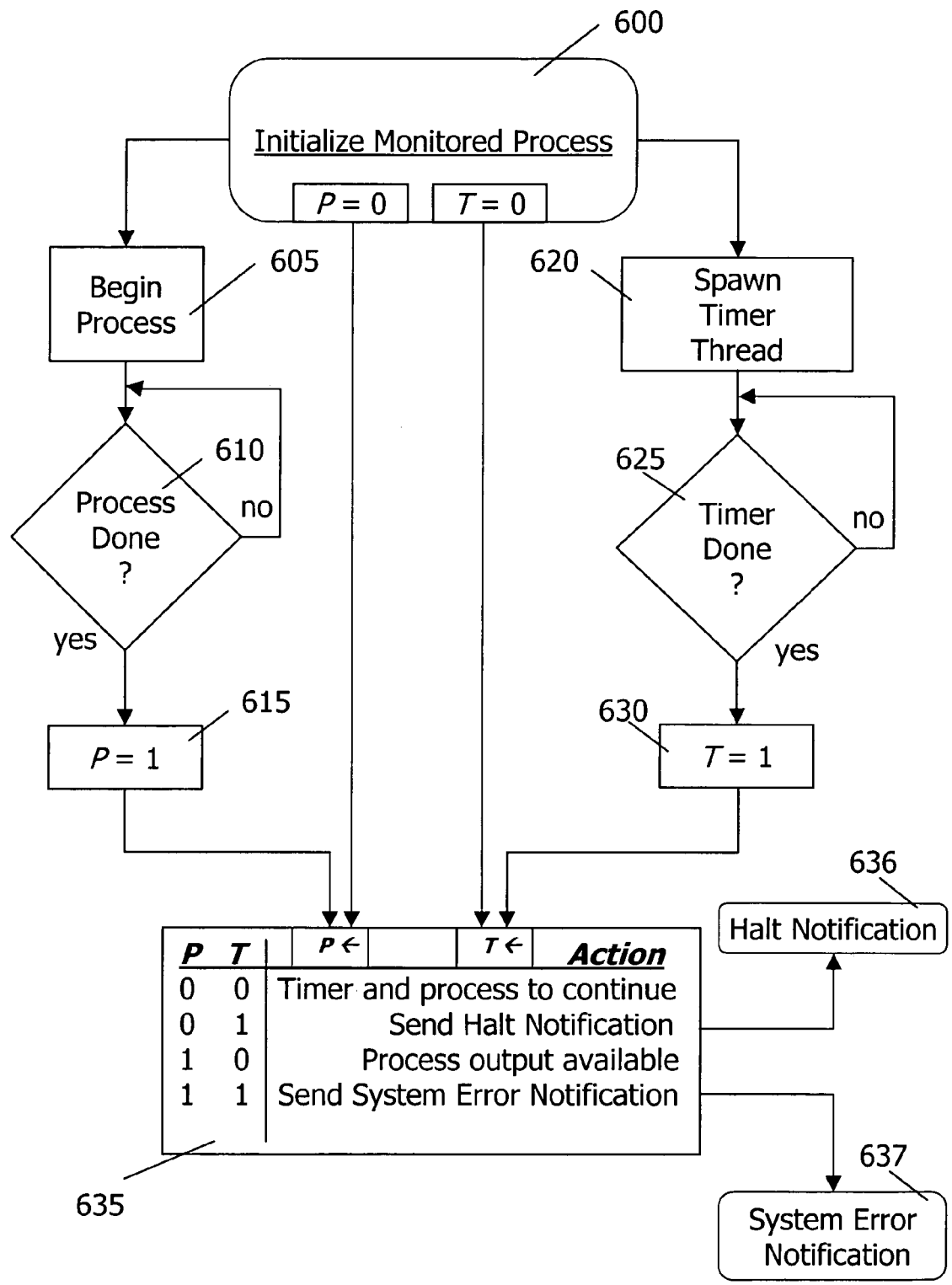
FIG. 4. is a flow chart illustrating a process for detecting a halted process.

Referring to FIG. 4, assume a monitored process is to be started on a host computer. Before the monitored process commences, two system variables, P and T, are initialized to predetermined values. Step 600 shows the variables P and T where P denotes the process complete variable, and T denotes the timer complete variable. Setting both variables to '0' in step 600 indicates neither the process nor the timer have completed. The process begins executing at Step 605 and a timer thread is spawned in step 620, both steps commencing at substantially the same time. Spawning a timer thread refers to launching an application that counts a predetermined amount of time before signaling that the amount of time has elapsed.

Step 610 tests for the condition of a completed process. If the process is not complete, the test is repeated. When the process completes, P is set to '1' in Step 615. Concurrent with the testing for a completed process, the timer is tested in Step 625. If the timer has not reached a predetermined value, the test is repeated. When the timer is complete, T is set to '1' in Step 630. Steps 620, 625 and 630 are equivalent to starting a program that will change the value of T to '1' after a predetermined time interval has elapsed. The time interval is set to be slightly longer than that typically required for the process to complete. The values of the status variables are substantially continuously monitored in Step 635.

Four possible combinations of the status variables are possible, as shown in the left hand side portion of Step 635. When both values are '0', no action is required as the process is running and the elapsed time counter has not yet reached the predetermined maximum value. When P equals '1' and T equals '0', the process has completed before the maximum time has elapsed. Therefore, the timer thread is killed and the outputs of the process are available for subsequent use. When P equals '0' and T equals '1', the timer has reached its maximum value before the process has completed. This condition indicates a halted process. Therefore, a halt notification 636 is sent to an operator. Finally, although it should not occur in normal operations, it is possible for both P and T to equal '1'. This event indicates some type of system error and would require operator attention. Therefore, a system error notification 637 is sent alerting an operator of this condition.

Halts in processing may be caused by a variety of problems. Two common problem areas are digitization and the CAD application. As long as the operating system of the computer 120 remains operable, notifications may be constructed and sent.

Halt Detection in Digitization Process

The method described in FIG. 4 is explained in terms of the film digitization process. According to the invention, process complete and timer variables P and T are initialized to '0', and then the request for image data is issued corresponding to step 605. When the host computer requests image data, the digitizer begins to feed a film through the film path with the object of creating digital image data. At substantially the same time, a timer thread is spawned. Assuming digitization of a single film requires approximately 45 seconds, the timer thread is specified to allow 60 seconds to elapse before setting T equal to '1'. The process 610 now corresponds to the digitization of a film and creating of corresponding image data. The expected outcome is that all requested image data are provided. In this event, the variables P and T will take on respective values of '1' and '0'. The process output is the image data. Thus at step 635 the image data is made available to subsequent processing steps, presumably analysis by CAD algorithms.

An example demonstrating the notification feature of the invention is now provided. Consider initializing variables P and T, requesting image data as above, and beginning the digitization step 605 and spawning a timer thread at substantially the same moment. Assume a film becomes jammed in the feed mechanism of the digitizer. In this situation, Step 630 will occur before Step 615. Therefore, the variables P and T will take on respective values of '0' and '1'. Correspondingly, Step 635 will send a halt notification. Of course, other situations may occur which cause a notification to be sent. One such example would be a loss of communication between the host computer and the digitizer.

Film digitizers are typically connected with a host computer and provide digital image data, low-level communications and internal error codes. These error codes may be interpreted and used in constructing a notification. Importantly, this invention allows for notifications of halted processing to be sent to operators in a timely fashion even when digitizers do not provide such error codes.

Notification

Figure 5:
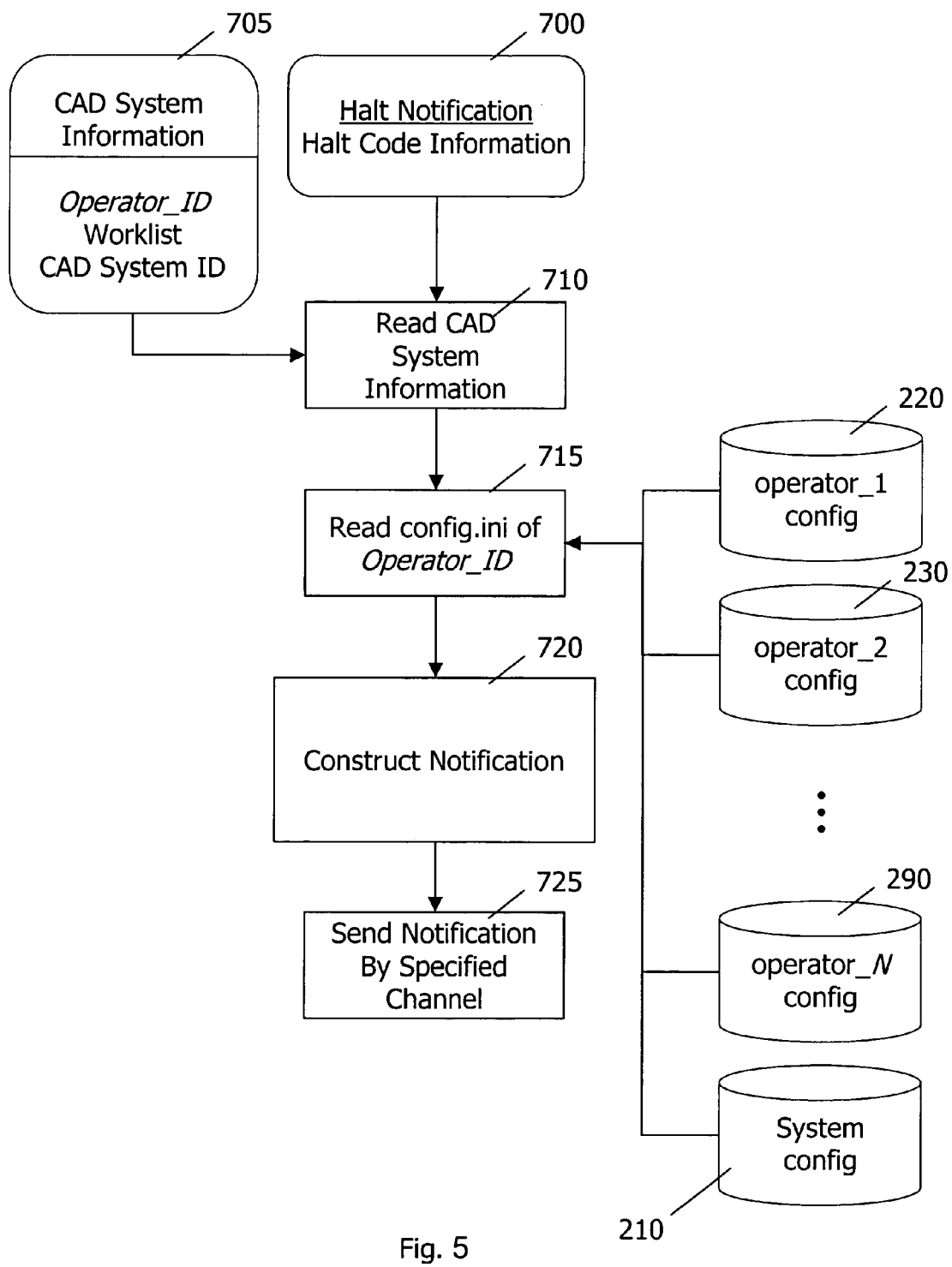
FIG. 5 is a flow chart illustrating a process for notifying a remotely located user.

Notifications are constructed as shown in FIG. 5. The notification process begins when a halt notification and associated halt code information are obtained, step 700. After the halt notification is received, CAD system information comprising CAD system identification, and worklist information 705, including operator identification, is read in Step 710. The operator identification is used to identify one or more associated configuration files, 220, 230, . . . , 290. Contents of the identified configuration files allow a customized notifications to be constructed in Step 720. The notifications are then transmitted by the channel or channels given in the configuration file.

The content of the notification varies according to operator settings specified in corresponding configuration files. Modes of notification comprise: caller ID only, message box, voice (text to speech applications are commercially available, for example WiViK, from Prentke Romich Company, Wooster, Ohio), text messaging, email including unformatted text and formatted hypertext, including html and xml documents.

With caller ID only notification, such as with a pager or some telephones, the operator receives a telephone call from the system, which is identified with a predetermined telephone number known to the operator. When the operator sees a call from the system, the operator will know that a halt in processing has occurred.

Operators may choose to be notified by a message box may displayed on their workstations or computing devices. In another embodiment, text messages can be transmitted to many phones, providing the operator with a description of the situation encountered by the CAD system. For example, the time of the error and the number of films remaining to be processed in the batch. An exemplary textual notification, 730, is provided in FIG. 6.

Corrective Action

If an operator is in the general vicinity of the CAD system and receives notification that CAD processing has halted, the operator may choose to go to the CAD system, correct the problem, and restart the digitizer from the console of the CAD system 100. When the operator is not in the general vicinity of the CAD system and receives notification of a processing halt on a mobile computing device or remote monitor and information regarding the type of error, it may be desirable for the operator to send commands to the system for restarting the digitizer. Commands to the system may be conveyed by a variety of means. Options include interacting with an interface provided on a remote display, calling a telephone number and interacting with a touch tone or speech recognition voice menu.

Alternatively, the configuration file may contain a field for automated error handling and an associated command stored in an automated error handling variable. For example, an operator may specify to automatically issue a "clear loaded film" command in the event an error code indicates a jammed film.

Additional Notifications

The modular design of the invention provides options for additional system functionality. An operator may desire notification when CAD results for a particular patient are available. In this situation, the operator selects a "notify upon completion" option for that patient in the CAD system worklist. Since case status and operator identification are available in the worklist, a notification is created and sent to a specific operator when the indicated case has been processed by the CAD system.

Another useful feature allows the operator to request a notification when a predetermined number of films remain to be processed. Such notification allows the operator to return to the digitization console for loading additional films to keep the CAD process running. In a preferred embodiment, a system config file stores a value for the number of remaining films at which a notification may be sent, N_low. The system config file is read by the CAD system when the batch process is initiated. Also, upon initiation of the batch process, worklist information is parsed to determine which operators are associated with the batch. The operator config files are then read for each associated operator. If the <low_film_warn> field is "yes" in an operator's config file, when the number of films remaining to be processed reaches the predetermined value, notification will be sent to that operator.

The running count of the number of films remaining to be processed is obtained from worklist information. The operator enters the number of films in each case as films are loaded. Therefore, the total number of films provided to the system is obtained by summing across the number of cases not yet processed. The running count of films is updated as each film is processed and as cases are added to the input. When a film has been successfully digitized, the count is decreased by one, and when a case is added, the film count is increased by the number of films in that case.

What is claimed is:

1. A method for providing remote monitoring of status information to a film-based CAD system user comprising:
   providing a CAD system with a film digitizer;
   providing films to be processed to the film digitizer;
   performing a processing operation on the films;
   identifying a status change in the digitizer during the processing operation; and
   transmitting notification of the status change to a user located remotely from the digitizer.

2. The method of claim 1 wherein the step of identifying a status change comprises identifying a delay in digitizing a film.

3. The method of claim 2 wherein the step of identifying a delay in digitizing a film comprises initiating a timing process at substantially the same moment as a process of digitizing a film begins and identifying a condition where processing of the film is not complete and the timing process has timed out.

4. The method of claim 2 including the step of the user transmitting a command to the CAD system from a remote location to continue processing of the films after receiving notification of the status change.

5. The method of claim 1 wherein the step of identifying a status change comprises identifying completion of a predetermined digitization operation.

6. The method of claim 5 wherein the completion of a predetermined digitization operation comprises completing digitization of the last case in a group of cases to be digitized.

7. The method of claim 5 including the step of the user inputting a request to the CAD system to be notified upon completion of the predetermined digitization operation.

8. The method of claim 1 wherein the step of identifying a status change comprises completion of a processing operation for a predetermined patient.

9. The method of claim 1 wherein the step of transmitting notification includes transmitting notification through a telephonic device.

10. The method of claim 9 wherein the telephonic device comprises a cellular telephone.

11. The method of claim 9 including the step of the user contacting the CAD system and obtaining additional information relating to the status change from the CAD system upon receiving notification of the status change.

12. The method of claim 11 including the step of the user transmitting a command via the telephone to the CAD system to take a corrective action for processing of the films after receiving notification of the status change.

13. The method of claim 1 wherein the step of transmitting notification includes transmitting notification through a paging device.

14. The method of claim 1 wherein the step of transmitting notification includes transmitting notification through a wireless connection to a mobile computing device.

15. The method of claim 14 wherein the notification comprises an electronic mail message.

16. The method of claim 14 wherein the step of transmitting notification further comprises displaying a message box on a screen of the mobile computing device.

17. The method of claim 1 wherein the step of transmitting notification includes transmitting notification to a monitor located remotely from the digitizer.

18. The method of claim 17 wherein the notification comprises an electronic mail message.

19. The method of claim 17 wherein the step of transmitting notification further comprises displaying a message box on the monitor.

20. The method of claim 1 wherein the step of transmitting notification comprises the CAD system accessing a configuration file containing information including user specific information.

21. The method of claim 20 wherein the user specific information includes phone numbers and predetermined user notification delivery preferences.

22. A method for operating a digitizer comprising:
providing a CAD system, the CAD system including a film digitizer and a user specific configuration file having information for initiating contact with a user;
providing films to be processed to the film digitizer;
performing a processing operation on the films;
identifying a status change in the digitizer during the processing operation; and
transmitting notification of the status change to a user located remotely from the digitizer.

23. The method of claim 22 wherein the step of identifying a status change comprises identifying a delay in digitizing a film.

24. The method of claim 22 wherein the step of transmitting notification comprises automatically initiating contact with the user.

25. The method of claim 24 wherein the step of automatically initiating contact with the user comprises the CAD system accessing a configuration file containing information including user specific information.

26. A method for providing remote monitoring of status information to a film-based CAD system user comprising:
providing a CAD system with a film digitizer;
providing films to be processed to the film digitizer;
performing a processing operation on the films;
identifying a status change in the digitizer during the processing operation; and
initiating contact with a user located remotely from the digitizer in response to the identification of a status change.

27. The method of claim 26 wherein the step of automatically initiating contact with the user comprises the CAD system accessing a configuration file containing information including user specific information.

28. A method for providing remote monitoring of status information to a CAD system user comprising:
providing input imagery to the CAD system;
performing a processing operation on the input imagery;
identifying a status change in the processing operation; and
transmitting notification of the status change to a user located remotely from the CAD system.

29. The method of claim 28 wherein the step of transmitting notification comprises automatically initiating contact with the user.

30. The method of claim 29 wherein the step of automatically initiating contact with the user comprises the CAD system accessing a configuration file containing information including user specific information.

31. The method of claim 30 wherein the user specific information comprises at least an internet access address or phone number for the user to receive an automatically generated message from the system.

\* \* \* \* \*